United States Patent [19]

Dalton et al.

[11] 4,071,528

[45] Jan. 31, 1978

[54] CERTAIN THIAZOLIDINE AND TETRAHYDROTHIAZINE COMPOUNDS

[75] Inventors: Sally Elizabeth Dalton, Brentwood; William George Gingell, Stondon Massey, near Brentwood; David Conwil Jenkins, Barkingside; Leslie George King, London; Glyn Evan Lee, Thorpe Bay; Garth Molesdale Thompson, Brentwood, all of England

[73] Assignee: May & Baker Limited, England

[21] Appl. No.: 736,170

[22] Filed: Oct. 27, 1976

[30] Foreign Application Priority Data

Oct. 29, 1975 United Kingdom ............ 44717/75

[51] Int. Cl.² ............ C07D 277/54; C07D 279/06
[52] U.S. Cl. ............ 260/306.7 T; 260/609 R; 560/16; 560/13; 424/170; 424/246; 424/270; 544/54
[58] Field of Search ............ 260/306.7 T, 243 R

[56] References Cited

U.S. PATENT DOCUMENTS 3,759,938  9/1973  Giraudon ............ 260/306.7 T

*Primary Examiner*—R. J. Gallagher
*Attorney, Agent, or Firm*—Stevens, Davis, Miller & Mosher

[57] ABSTRACT

Benzene derivatives of the formula:

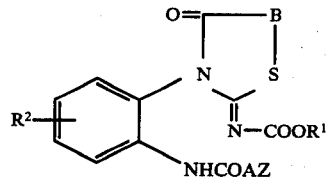

wherein $R^1$ is alkyl, $R^2$ is a group $—SR^3$, $—SOR^3$, $—SO_2R^3$ or $—OR^3$, in which $R^3$ is alkyl, cycloalkyl, alkenyl, alkynyl, aralkyl, aryl or cycloalkylalkyl, whose position on the benzene ring is either para to $—NHCOAZ$ or para to the heterocyclo group, A is a $C_{1-4}$ aliphatic hydrocarbon radical, B is a bivalent methylene or ethylene group, and Z is a primary, secondary or tertiary amino group, and acid addition salts and quaternary ammonium derivatives thereof, are new compounds useful as anthelmintics and antifungal agents.

17 Claims, No Drawings

CERTAIN THIAZOLIDINE AND TETRAHYDROTHIAZINE COMPOUNDS

This invention relates to benzene derivatives, compositions containing them and their use as anthelmintics and antifungal agents.

As a result of research and experimentation, it has been found that the new benzene derivatives of the general formula:

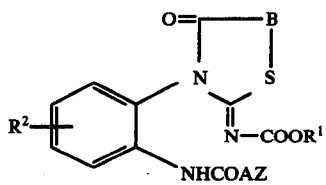

I wherein $R^1$ represents a straight- or branched-chain alkyl group containing from 1 to 4 carbon atoms (preferably methyl), $R^2$ represents a group of the formula $-SR^3$, $-SOR^3$, $-SO_2R^3$ or $-OR^3$ [wherein $R^3$ represents a straight- or branched-chain alkyl group containing from 1 to 6 carbon atoms, e.g. methyl or ethyl, a cycloalkyl group containing from 3 to 7 carbon atoms, e.g. cyclopentyl or cyclohexyl, a straight- or branched-chain alkenyl or alkynyl group containing from 3 to 6 carbon atoms, e.g. allyl or prop-2-ynyl, an aralkyl, e.g. phenylalkyl, group with 1 or 2 carbon atoms in the alkyl moiety, for example benzyl, or $R^3$ represents an aryl, e.g. phenyl, group which may optionally be substituted by a halogen (e.g. chlorine) atom or by a straight- or branched-chain alkyl or alkoxy group containing from 1 to 3 carbon atoms, or represents a cycloalkylalkyl group in which the cycloalkyl moiety contains from 3 to 7 carbon atoms and the alkyl moiety contains 1 or 2 carbon atoms, e.g. cyclohexylmethyl] whose position on the benzene ring is either para to the group —NHCOAZ or, preferably, para to the heterocyclo group shown in formula I, A represents a bivalent straight-chain aliphatic hydrocarbon radical containing from 1 to 4 carbon atoms which may be saturated or unsaturated (e.g. a methylene, polymethylene, e.g. ethylene, or vinylene radical) and which may optionally be substituted by at least one methyl group, Z represents a group of the general formula:

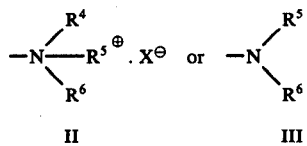

II    III wherein $R^4$ represents a hydrogen atom or a straight- or branched-chain alkyl group containing from 1 to 4 carbon atoms, e.g. methyl or ethyl, $R^5$ represents a hydrogen atom or a straight- or branched-chain alkyl group containing from 1 to 4 carbon atoms, e.g. methyl or ethyl, or a phenylalkyl group with 1 or 2 carbon atoms in the alkyl moiety, e.g. benzyl, and $R^6$ represents a hydrogen atom or a straight- or branched-chain alkyl group containing from 1 to 4 carbon atoms, e.g. methyl or ethyl, or $R^5$ and $R^6$ together with the nitrogen atom to which they are attached form a 5-, 6- or 7-membered heterocyclic ring which may contain in the ring one or two further hetero atoms selected from oxygen, nitrogen and sulphur, and which may optionally be substituted by one or more straight- or branched-chain alkyl groups each containing from 1 to 6 carbon atoms, for example a pyrrolidin-1-yl, piperidino, morpholino, piperazin-1-yl or 4-alkylpiperazin-1-yl, e.g. 4-methylpiperazin-1-yl, group, $X^-$ represents a pharmaceutically acceptable or agriculturally acceptable anion, and B represents a bivalent methylene or ethylene group which may optionally be substituted by at least one methyl group, possess valuable chemotherapeutic properties, having, in particular, high anthelmintic and anti-fungal activity.

When the compounds of general formula I can exist in stereoisomeric forms, all such isomers and their mixtures and racemates are included within the scope of the present invention.

The term 'pharmaceutically acceptable anion' means an anion which is relatively innocuous to the animal organism when used in therapeutic doses so that the beneficial properties of the cation are not vitiated by side-effects ascribable to the anion.

The term 'agriculturally acceptable anion' means an anion which is generally regarded as acceptable for use in agricultural practice, being relatively innocuous to the vegetable organism when used at fungicidal rates of application, so that the beneficial properties of the cation are not vitiated by side-effects ascribable to that anion.

Good examples of anions within the definition of $X^-$ are halide ions (e.g. chloride, bromide and iodide ions) and the methanesulphonate, sulphate, nitrate, phosphate, acetate, citrate, propionate, succinate, benzoate, fumarate, maleate, tartrate, theophyllinacetate, salicylate, phenolphthalinate, methylene-bis-$\beta$-hydroxy-naphthoate, amsonate and isethionate ions.

Compounds of formula I wherein Z represents a group of formula II ($R^1$, $R^2$, $R^4$, $R^5$, $R^6$, A, B and $X^-$ being as hereinbefore defined) are particularly valuable because of their solubility in water, especially such compounds wherein $X^-$ represents a chloride or methanesulphonate ion.

Another class of particularly valuable compounds of formula I are those wherein $R^1$ represents an ethyl or, preferably, methyl group, $R^2$ represents a group of the formula $-SOR^{3'}$ or, preferably, $-SR^{3'}$ (wherein $R^{3'}$ represents a straight- or branched-chain alkyl group containing from 1 to 6, preferably 1 to 3, carbon atoms, or an allyl, phenyl, benzyl, cyclopentyl or cyclohexylmethyl group), A represents a methylene or ethylene group, B represents a methylene group, $R^4$ (when present) represents a hydrogen atom, $R^5$ and $R^6$ represent methyl or ethyl groups, and $X^-$ (when present) is as hereinbefore defined, preferably representing a chloride or methanesulphonate ion.

Compounds of formula I of outstanding importance are those wherein $R^1$ represents a methyl group, $R^2$ represents a phenylthio or ethylthio group, A represents a methylene group, B represents a methylene group, $R^4$ (when present) represents a hydrogen atom, $R^5$ and $R^6$ represent methyl or ethyl groups, and $X^-$ (when present) is as hereinbefore defined.

Among individual compounds of formula I of particular importance are the following:

A. 3-[2-(2-dimethylaminoacetamido)-4-phenylthiophenyl]-2-methoxycarbonyliminothiazolidin-4-one,
B. 3-[4-allylthio-2-(2-dimethylaminoacetamido)phenyl]-2-methoxycarbonyliminothiazolidin-4-one, C. 3-[4-ethylthio-2-(2-dimethylaminoacetamido)-phenyl]-2-methoxycarbonyliminothiazolidin-4-one, D. 3-[2-(2-diethylaminoacetamido)-4-phenylthio-phenyl]-2-methoxycarbonyliminothiazolidin-4-one, E. 3-[2-(2-dimethylaminoacetamido)-5-phenylthio-phenyl]-2-methoxycarbonyliminothiazolidin-4-one, F. 3-[4-cyclohexylmethylthio-2-(2-dimethylaminoacetamide)phenyl]-2-methoxycarbonyliminothiazolidin-4-one, G. 3-[4-n-butylthio-2-(2-dimethylaminoacetamido)-phenyl]-2-methoxycarbonyliminothiazolidin-4-one, H. 3-[4-benzylthio-2-(2-dimethylaminoacetamido)-phenyl]-2-methoxycarbonyliminothiazolidin-4-one, I. 3-[4-cyclopentylthio-2-(2-dimethylaminoacetamido)-phenyl]-2-methoxycarbonyliminothiazolidin-4-one, J. 3-[2-(2-dimethylaminoacetamido)-4-n-pentylthio-phenyl]-2-methoxycarbonyliminothiazolidin-4-one, K. 3-[2-(2-dimethylaminoacetamido)-4-n-propylthio-phenyl]-2-methoxycarbonyliminothiazolidin-4-one, and L. 3-[2-(3-dimethylaminopropionamido)-4-phenylthio-phenyl]-2-methoxycarbonyliminothiazolidin-4-one, especially compounds A, C, D and E, and their salts, for example their hydrochlorides and methanesulphonates.

The letters of the alphabet A to L are assigned to the compounds for easy reference later in the specification, for example in the following Tables.

The compounds of general formula I are valuable anthelmintics, useful for the treatment of helminth infections in man and domestic animals, for example cattle, sheep, pigs, goats, poultry and equines, for example infections of the gastro-intestinal tract caused by parasitic nematode worms, for example members of the family Trichostrongylidae, and infections by parasitic trematodes of the genus Fasciola (e.g. *Fasciola hepatica*, otherwise known as liver flukes) in domestic animals.

The value of the compounds of formula I as anthelmintics has been demonstrated, for example, in the following tests.

In the Tables of results "s.c." means subcutaneous and the doses are expressed in mg/kg animal body weight.

Where it is indicated that a compound was administered by the subcutaneous route, it was administered in the form of an aqueous solution of the methanesulphonate salt, prepared by treatment of the free base with aqueous methanesulphonic acid solution (0.2N) in equimolecular proportions, followed by dilution with water to a convenient volume for administration.

A. Activity against roundworms in rats

A.1. Rats were infected with 100 *Nippostrongylus brasiliensis* larvae each, by the subcutaneous route. After 6 days, when the infection was patent, the rats were randomised and allotted to groups of 5 animals each, ready for treatment. One group was used for each dose level of the test compound, which was administered by the oral or subcutaneous route, and in each experiment, one group of 10 animals was left untreated as a control. All the rats were killed for post-mortem worm counts 48 hours after treatment.

The activities, expressed in terms of the percentage reduction in mean worm load of the treated groups compared with the untreated group, are shown in Table I.

TABLE I

| Compound | Route of Administration | Dose | % Reduction of mean worm load |
|---|---|---|---|
| A | oral | 100 | 99 |
| B | oral | 100 | 97 |
| B | s.c. | 100 | 90 |
| C | oral | 100 | 74 |
| C | s.c. | 100 | 89 |
| D | oral | 100 | 99 |
| D | s.c. | 100 | 88 |
| E | oral | 100 | 65 |
| E | s.c. | 100 | 54 |
| G | oral | 100 | 96 |
| G | s.c. | 100 | 84 |
| J | oral | 100 | 59 |
| K | oral | 50 | 99 |
| K | s.c. | 50 | 96 |
| L | oral | 100 | 90 |

A.2. Rats were infected with 100 *Nippostrongylus brasiliensis* larvae each, by the subcutaneous route. After 24 hours the rats were randomised and allotted to groups of 5 animals each, ready for treatment. Doses of the test compound were then administered to each group by the oral or subcutaneous route, one group of 10 animals being left untreated as a control. All the rats were killed for post-mortem worm counts 6 days after dosing. The activities, expressed in terms of the percentage reduction in mean worm load of the treated groups compared with the untreated control group, are given below in Table II.

TABLE II

| Compound | Route of Administration | Dose | % Reduction of mean worm load |
|---|---|---|---|
| A | oral | 50 | 99 |
|   |   | 12.5 | 85 |
| A | s.c. | 50 | 99 |
|   |   | 12.5 | 91 |
| B | oral | 50 | 98 |
| B | s.c. | 50 | 97 |
| C | oral | 50 | 90 |
|   |   | 12.5 | 81 |
| C | s.c. | 50 | 98 |
|   |   | 12.5 | 86 |
| D | oral | 50 | 98 |
|   |   | 12.5 | 96 |
| D | s.c. | 50 | 100 |
|   |   | 25 | 96 |
| E | oral | 50 | 95 |
| E | s.c. | 50 | 99 |
| F | oral | 100 | 59 |
| F | s.c. | 100 | 46 |
| G | oral | 50 | 98 |
|   |   | 12.5 | 95 |
| G | s.c. | 50 | 100 |
|   |   | 12.5 | 96 |
| I | oral | 100 | 96 |
|   |   | 25 | 97 |
| I | s.c. | 100 | 99 |
|   |   | 25 | 87 |
| J | oral | 100 | 99 |
|   |   | 50 | 99 |
| J | s.c. | 100 | 99 |
|   |   | 50 | 99 |
| K | oral | 50 | 97 |
|   |   | 3.125 | 92 |
| K | s.c. | 50 | 98 |
|   |   | 3.125 | 96 |
| L | oral | 50 | 81 |
| L | s.c. | 50 | 90 |

B. Activity against roundworms in sheep

B.1. Activity against *Haemonchus contortus* and *Nematodirus spathiger* in their adult stages in lambs.

Worm-free, 8–10 week old lambs were each infected with 5000 *H. contortus* and 15000 *N. spathiger* larvae. Approximately 3 weeks later, doses of test compound A were administered to each group of 2 animals, by the subcutaneous route, one group of 2 animals being left untreated as a control.

Individual faecal *H. contortus* egg counts were determined 1 day before and 5–7 days after treatment, when all the lambs were killed for post-mortem worm counts. The activities, expressed in terms of the percentage reduction in mean worm burden of each worm species compared with the untreated control group, are given below.

Compound A at a subcutaneous dose of 10 mg/kg animal body weight produced a 100% reduction of the mean worm burden of *H. contortus* and a 99% reduction of the mean worm burden of *N. spathiger*.

B.2. Activity against *Haemonchus contortus, Ostertagia circumcincta, Trichostrongylus axei, Trichostrongylus colubriformis* and *Nematodirus spathiger* in their 4th larval and adult stages in lambs.

Worm-free, 8–10 week old lambs were each infected with 5,000 *H. contortus*, 15,000 *O. circumcincta*, 20,000 *T. axei*, 15,000 *T. colubriformis* and 15,000 *N. spathiger* larvae.

Doses of test compound A of 4 mg/kg animal body weight were then administered to each group of 2 animals, by the oral route, after 7 days or 25 days to examine the effects against the 4th larval stage and mature adult worms respectively, one group of 2 animals being left untreated as a control. All the lambs were killed for post-mortem worm wounts 28 days after infection. The activities, expressed in terms of the percentage reduction in mean worm burden of each worm species compared with the untreated control group, are given below in Table III.

TABLE III

| Age of infection when treated (days) | Percentage reduction in mean worm burdens | | | | |
|---|---|---|---|---|---|
| | *H. contortus* | *O. circumcincta* | *T. axei* | *T. colubriformis* | *N. spathiger* |
| 7 | 100 | 99 | 100 | 100 | 95 |
| 25 | 100 | 100 | 100 | 100 | 97 |

C. Activity against roundworms in calves

C.1. Activity against *Cooperia oncophora* and *Ostertagia ostertagi* in their adult stages in calves.

Worm-free, 6–7 week old calves were each infected with 15,000 *C. oncophora* and 15,000 *O. ostertagi* larvae. Approximately 3 weeks later, doses of the test compound were administered to each group of 2 animals by the subcutaneous route, one group of two animals being left untreated as a control.

Individual faecal egg counts were determined 1 day before treatment and 5–7 days after treatment.

The activities, expressed in terms of the mean percentage reduction in egg count, are shown in Table IV.

TABLE IV

| Compound | Dose | % Reduction of mean egg count |
|---|---|---|
| B | 15 | 44 |
| C | 15 | 100 |
| D | 15 | 98 |
| E | 15 | 100 |
| F | 25 | 50 |
| K | 15 | 85 |
| L | 15 | 84 |

C.2. Activity against *Cooperia oncophora, Ostertagia ostertagi*, and *Dictyocaulus viviparus* in their mature and immature stages in calves.

Worm free, 6–7 week old calves were each infected with 15,000 *C. oncophora*, 15,000 *O. ostertagi* and 3,000 *D. viviparus* larvae. Groups of two animals each were treated subcutaneously with test compound A at a dose of 25 mg/kg animal body weight at 7 days or 25 days after infection, one group of two animals being left untreated as a control. All calves were killed approximately 28 days after infection and were examined for residual worm burdens. The percentage reduction in mean worm burden of each worm species compared with the untreated control group is given below in Table V.

TABLE V

| Age of Infection on Treatment | % Reduction of mean worm burdens | | |
|---|---|---|---|
| | *C. oncophora* | *O. ostertagi* | *D. viviparus* |
| 7 days | 100 | 97 | 83 |
| 25 days | 100 | 100 | 82 |

D. Activity against mature and immature liver flukes in sheep

On the first day of the experiment a group of sheep were each infected with 300 metacercariae of liver fluke *Fasciola hepatica* and on the 56th day they were each infected with a further 300 metacercariae of *F. hepatica*.

On day 70 of the experiment, doses of the test compounds of 25 mg/kg animal body weight were administered orally in gelatin capsules to groups of two animals per compound. One group of two animals was left untreated as controls. On day 98 of the experiment, all the sheep were killed. The number of mature flukes present in the bile ducts and the numbers of immature flukes present in the rest of the liver were counted.

The activities, expressed in terms of the percentage reduction in mean fluke burdens compared with the untreated controls, are shown below in Table VI.

TABLE VI

| Compound | Mean % Reduction | |
|---|---|---|
| | Mature flukes | Immature flukes |
| A | 93 | 29 |
| C | 72 | 85 |
| D | less than 50 | 75 |

The utility of the compounds of formula I as anthelmintics is enhanced by the fact that they are relatively harmless to mammals, demonstrated by the following test.

Mice were each treated orally with one of the compounds of formula I, and they were observed during the next 6 days. The LD50 figures obtained (doses lethal to 50% of mice tested) are shown in Table VII, expressed in mg/kg animal body weight.

TABLE VII

| Compound | A | B | C | D | E |
|---|---|---|---|---|---|
| LD50 | ~1000 | >1000 | >1000 | >1000 | >1000 |
| Compound | G | I | J | K | L |
| LD50 | >1000 | >1000 | >1000 | >1000 | >1000 |

The symbol "~" means "about" and ">" means "greater than".

In addition to possessing anthelmintic activity, the new compounds of general formula I are also useful as agricultural pesticides, in particular as fungicides against species of fungi which are pathogenic to plants, and are also active as fungicides against fungal species which are pathogenic to animals.

For example, the compounds of formula I are of particular utility in fungicidal seed dressings, for example seed dressings for the protection of cereal seeds, and are also useful in combating grey moulds (e.g. *Botrytis* spp.) and brown moulds and storage rots of fruit and vegetables, for example grapes, peaches, lettuces and beans.

As fungicides for use against species of fungi pathogenic to plants, the compounds of formula I are particularly useful in the control of *Alternaria solani, Botrytis cinerea, Cercospora beticola, Cochliobolus sativus, Colletotrichum* spp., e.g. *C. gassypii, Fusarium* spp., e.g. *F. nivalae* and *F. roseum, Gloeosporium* spp., *Helminthosporium* spp., e.g. *H. avenae* and *H. gramineum, Mycosphaerella* spp., e.g. *M. pinodes* and *M. pomi, Nectria* spp., *Penicillium* spp., *Piricularia oryzae, Pythium* spp., *Rhizoctonia* spp., *Rhizopus nigricans, Sclerotinia* spp., e.g. *S. cinerea* and *S. sclerotiorum, Septoria nodurum, Tilletia caries, Ustilago avenae, Venturia inaequalis* and *Verticillium* spp., e.g. *V. alboatrum*.

The value of the compounds of formula I as fungicides has been demonstrated, for example, in the following test.

Test tubes containing 4.0 ml of molten potato dextrose agar at about 50° C were inoculated with 0.5 ml of suspension of test compound and 0.5 ml of fungal suspension delivered from a sterile syringe to give a final concentration of each compound of 50, 10 or 2 ppm. Two replicate tubes were inoculated with each fungal species. After the addition of test compounds and fungal inoculum to the molten medium the tubes were sloped and the agar was allowed to set. The tubes were incubated at 25° C for either 2 days (*Mycosphaerella pinodes*) or 3 days (*Helminthosporium avenae*).

The minimum effective concentrations of two typical compounds of formula I, i.e. the minimum concentrations which totally inhibit fungal growth, are given in Table VIII.

The suspensions of test compounds were prepared by grinding 0.025 g of test compound with sterile distilled water containing 0.1 ml of 0.1% Texofor FX170 wetting agent, followed by dilution to the concentration desired.

The inoculum of *Mycosphaerella pinodes* was prepared as follows:

A one to two week old culture on Coon's agar on plates was scraped off with a glass rod and sterile distilled water and filtered through muslin. The filtrate, containing the spores, was used for inoculation.

The inoculum of *Helminthosporium avenae* was prepared as follows:

A culture of H. avenae on oatmeal agar was inoculated into Czapek Dox broth. Two weeks later the broth was macerated to give a fine suspension containing mycelia, for use in inoculation.

TABLE VIII

| Compound | Minimum effective concentration | |
|---|---|---|
| | M. pinodes | H. avenae |
| A | less than 2 ppm. | between 2 and 10 ppm. |
| E | less than 2 ppm. | between 10 and 50 ppm. |

According to a feature of the present invention, compounds of formula I are prepared by the suitable adaptation of known methods, for example, (1) by the reaction of compounds of the general formula:

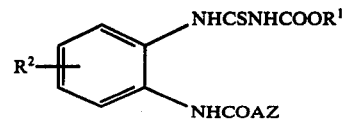

(wherein $R^1$, $R^2$, A and Z are as hereinbefore defined) with a compound of the general formula:

$$X^1BCOX^2 \qquad V$$

wherein B is as hereinbefore defined, and $X^1$ and $X^2$ are the same or different and each represents a halogen (preferably chlorine) atom. In general, the reaction is carried out in a polar organic solvent, e.g. N-methylpyrrolid-2-one or dimethylformamide, optionally in the presence of an alkaline condensation agent, e.g. N,N-dimethylaniline, and at a temperature between 0° C and 80° C.

This process is particularly useful for the preparation of compounds of formula I wherein Z is a grouping of formula II or III and $R^5$ and $R^6$ are other than hydrogen atoms and $X^-$, when present, is a halide (preferably chloride) ion, $R^1$, $R^2$, A and B being as hereinbefore defined.

(2) by the reaction of a compound of the general formula:

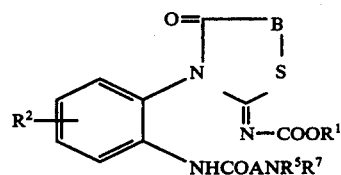

wherein A, $R^1$, $R^2$, $R^5$ and B are as hereinbefore defined, and $R^7$ is a suitable protecting group, e.g. benzyloxycarbonyl, with a reagent for removing the said protecting group, e.g. a solution of hydrogen bromide in glacial acetic acid, to give a compound of formula I wherein $R^6$ (in the definition of Z) represents a hydrogen atom, the various other symbols being as hereinbefore defined.

(3) by the reaction of a compound of formula I, wherein $R^1$, $R^2$, A and B are as hereinbefore defined and Z represents a group of formula III (wherein $R^5$ and $R^6$ are as hereinbefore defined) with a compound of the general formula:

$$R^4X^3 \qquad VII$$

(wherein $R^4$ is as hereinbefore defined and $X^3$ is an atom or group corresponding to the anion $X^-$) to give a compound of formula I wherein $R^1$, $R^2$, A and B are as hereinbefore defined and Z is a group of formula II, wherein $R^4$, $R^5$ and $R^6$ are as hereinbefore defined and the axion $X^-$ is derived from the atom or group represented by the symbol $X^3$ in the compound of formula VII.

The reaction is preferably carried out in an inert organic solvent, for example ethanol, ethyl acetate, acetone or diethyl ether, at a temperature between 10° C and 40° C.

Alternatively, the reaction may be carried out in an aqueous medium. This method is particularly useful when the compound of formula VII is an acid, i.e. $R^4$ represents a hydrogen atom. By this method there is generally obtained an aqueous solution of the desired salt.

(4) by treatment of a compound of formula I wherein Z represents a group of formula II wherein $R^4$ represents a hydrogen atom ($R^1$, $R^2$, $R^5$, $R^6$, A, B and $X^-$ being as hereinbefore defined) with a base to give a compound of formula I wherein $R^1$, $R^2$, A and B are as hereinbefore defined and Z represents a group of formula III.

The reaction is preferably carried out by means of a carbonate or hydroxide of an alkali metal, e.g. sodium carbonate, in the presence of water, generally at room temperature.

Alternatively, the reaction may be carried out by treatment with a strong organic base, e.g. triethylamine, in an organic medium, e.g. methanol.

Optionally the reaction may be carried out in situ without isolation of the compound of formula I wherein Z represents a group of formula II from the reaction mixture in which it is produced by means of one of the reactions hereinbefore described.

Compounds of formula IV may be prepared, for example, (i) by the reaction of equimolecular quantities of an isothiocyanate of the general formula:

  VIII (wherein $R^1$ is as hereinbefore defined) and an amine of the general formula:

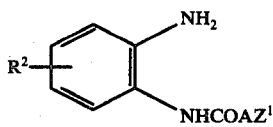  IX (wherein $R^2$ and A are as hereinbefore defined and $Z^1$ represents a group of formula II, wherein $R^5$ and $R^6$ are as hereinbefore defined, $R^4$ represents a hydrogen atom and $X^-$ represents a halide ion, or of formula III as hereinbefore defined) to give a compound of formula IV wherein $R^1$, $R^2$ and A are as hereinbefore defined, and Z represents the group $Z^1$ as hereinbefore defined (hereinafter referred to as "compounds of formula IVa").

The reaction may be carried out in the presence of an inert solvent, for example an alkanone containing from 3 to 5 carbon atoms, e.g. acetone or methyl ethyl ketone, an alkanol containing from 1 to 4 carbon atoms, e.g. methanol or ethanol, dioxan, ethyl acetate, acetonitrile or an aromatic hydrocarbon, e.g. toluene, at a temperature between 0° C and 150° C and preferably between 10° C and 60° C, and optionally in the presence of acetic acid.

The isothiocyanates of formula VIII may be prepared by the reaction of an ester of the general formula:

  X (wherein $R^1$ and $X^1$ are as hereinbefore defined) and a thiocyanate of the general formula:

  XI wherein M is a metal, preferably an alkali metal or an alkaline earth metal, atom and q is the valency of that metal. The reaction may be carried out in the presence of an inert organic solvent, for example an alkanone containing from 3 to 5 carbon atoms, e.g. acetone, ethyl acetate or acetonitrile, at a temperature between 0° C and 100° C and preferably between 20° C and 60° C.

The preparation of compounds of formula VIII may be effected in situ for subsequent reaction with compounds of formula IX or, if desired, the compounds of formula VIII may be isolated by known methods prior to reaction with compounds of formula IX.

(ii) by the reaction of an amine of the general formula:

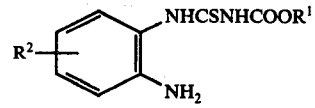  XII (wherein $R^1$ and $R^2$ are as hereinbefore defined) with a compound of the general formula:

  XIII (wherein $X^1$ and A are as hereinbefore defined, and $Z^2$ represents a group $Z^1$ as hereinbefore defined with the exception that neither $R^5$ nor $R^6$ can represent a hydrogen atom) to give a compound of formula IV wherein $R^1$, $R^2$ and A are as hereinbefore defined and Z represents the group $Z^2$ as hereinbefore defined (hereinafter referred to as "compounds of formula IVb").

The reaction is preferably carried out in an organic solvent, e.g. toluene or dimethylformamide, at a temperature between 0° C and the reflux temperature of the reaction mixture.

The compounds of formula XIII may be prepared by the reaction of a compound of the general formula:

  XIV (wherein A and $Z^2$ are as hereinbefore defined) with a reactive acid halide, e.g. phosphorus pentachloride. If desired, the compounds of formula XIII may be prepared in situ.

(iii) by the reaction of an amine of general formula XII (wherein $R^1$ and $R^2$ are as hereinbefore defined) with a compound of formula XIV (wherein A and $Z^2$ are as hereinbefore defined) in the presence of a condensing agent, e.g. phosphorus oxychloride, in a suitable solvent, e.g. dimethylformamide or dichloromethane, at a temperature between 0° C and the reflux temperature of the reaction mixture, to give a compound of formula IVb.

(iv) by reaction of a compound of the general formula:

  XV (wherein $R^1$, $R^2$, A and $X^1$ are as hereinbefore defined) with (a) a compound of the general formula:

  XVI (wherein $R^5$ and $R^6$ are as hereinbefore defined) an excess of which may be employed as an acid-binding agent, to give a compound of formula IVa, or (b) a compound of the general formula:

$$NR^{4'}R^5R^6 \quad \text{XVII}$$

(wherein $R^5$ and $R^6$ are as hereinbefore defined, and $R^{4'}$ represents a straight- or branched-chain alkyl group containing from 1 to 4 carbon atoms) to give a compound of formula IV wherein $R^1$, $R^2$ and A are as hereinbefore defined and Z is a group of formula II wherein $R^4$ is a straight- or branched-chain alkyl group containing from 1 to 4 carbon atoms, $R^5$ and $R^6$ are as hereinbefore defined and the anion $X^-$ is a halide ion derived from the halogen atom represented by $X^1$ in the compound of formula XV.

The reaction between the compound of formula XV and the compound of formula XVI may be carried out in an inert organic solvent, for example an alkanol containing from 1 to 4 carbon atoms, e.g. ethanol, or an aromatic hydrocarbon, e.g. benzene or toluene, at a temperature between 20° C and 100° C, preferably at room temperature or at the reflux temperature of the reaction mixture.

The reaction between the compound of formula XV and the compound of formula XVII may be carried out in an inert organic solvent, for example ethyl acetate or diethyl ether, at a temperature between 20° C and 80° C, and preferably at the reflux temperature of the reaction mixture.

(v) by the reaction of a compound of formula IV, wherein $R^1$, $R^2$ and A are as hereinbefore defined and Z represents a group of formula III (wherein $R^5$ and $R^6$ are as hereinbefore defined) with a compound of formula VII (wherein $R^4$ is as hereinbefore defined and $X^3$ is an atom or group corresponding to the anion $X^-$) to give a compound of formula IV wherein $R^1$, $R^2$ and A are as hereinbefore defined and Z is a group of formula II, wherein $R^4$, $R^5$ and $R^6$ are as hereinbefore defined and the anion $X^-$ is derived from the atom or group represented by the symbol $X^3$ in the compound of formula VII. The reaction is preferably carried out in conditions similar to those hereinbefore described for the reaction of compounds of formula I with compounds of formula VII.

(vi) by treatment of a compound of formula IV wherein Z represents a group of formula II wherein $R^4$ represents a hydrogen atom ($R^1$, $R^2$, $R^5$, $R^6$, A and $X^-$ being as hereinbefore defined) with a base, to give a compound of formula IV wherein $R^1$, $R^2$ and A are as hereinbefore defined and Z represents a group of formula III.

The reaction is preferably carried out in the conditions hereinbefore described for the reaction of compounds of formula I, wherein Z represents a group of formula II, with bases.

Compounds of formula VI may be prepared by the reaction together of compounds of the general formula:

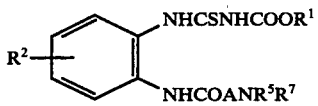

XVIII (wherein A, $R^1$, $R^2$, $R^5$ and $R^7$ are as hereinbefore defined) and compounds of formula V, preferably under the reaction conditions hereinbefore described for the reaction together of compounds of formula IV and compounds of formula V.

Compounds of formula IX may be prepared by the reduction of compounds of the general formula:

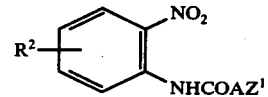

XIX (wherein $R^2$, A and $Z^1$ are as hereinbefore defined) by known methods for the reduction of aromatic nitro groups to amino groups, for example by hydrogenation in the presence of a hydrogenation catalyst, e.g. platinum or palladium, or by the use of ferrous chloride and reduced iron powder.

Compounds of formula XIX may be prepared by the reaction of a compound of the general formula:

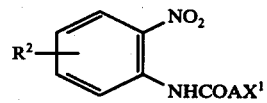

XX (wherein $R^2$, A and $X^1$ are as hereinbefore defined) with a compound of formula XVI, an excess of which may be employed as an acid-binding agent, under the conditions hereinbefore described for the reaction of compounds of formula XV with compounds of formula XVI.

Compounds of formula XX may be prepared by the reaction of a compound of the general formula:

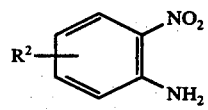

XXI (wherein $R^2$ is as hereinbefore defined) with a compound of the general formula:

$$X^1COAX^1 \quad \text{XXII}$$

wherein A and $X^1$ are as hereinbefore defined. The reaction is preferably carried out in an inert organic solvent, for example an alkanone containing from 3 to 5 carbon atoms, e.g. acetone, or an aromatic hydrocarbon, e.g. toluene, at a temperature between 0° C and 110° C.

Compounds of formula IX, wherein $R^2$, A and $Z^1$ are as hereinbefore defined, may be prepared from compounds of the general formula:

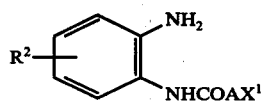

XXIII (wherein $R^2$, A and $X^1$ are as hereinbefore defined) by the application of processes hereinbefore described for the preparation of compounds of formula IV from compounds of formula XV.

Compounds of formula XXIII may be prepared by the reduction of compounds of formula XX by known methods for the reduction of aromatic nitro groups, for example as hereinbefore described for the reduction of compounds of general formula XIX.

Compounds of formula XV may be prepared by the reaction of a compound of formula XXIII with an isothiocyanate of formula VIII. The reaction may be carried out under the conditions hereinbefore described for the reaction of compounds of formula VIII with compounds of formula IX to give compounds of formula IV.

Compounds of formula XV may alternatively be prepared by the reaction of a compound of formula XII with a compound of formula XXII. The reaction may be carried out under the conditions hereinbefore described for the reaction of compounds of formula XXI with compounds of formula XXII to give compounds of formula XX.

Compounds of formula XVIII may be prepared (a) by reaction of an amine of formula XII with a compound of the general formula:

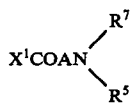   XXIV wherein A, R$^5$, R$^7$ and X$^1$ are as hereinbefore defined. The reaction is preferably carried out in an organic solvent, e.g. dimethylformamide, at a temperature between 0° C and the reflux temperature of the reaction mixture.

Compounds of formula XXIV may be prepared by the reaction of a compound of the general formula:

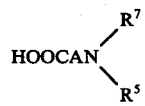   XXV (wherein A, R$^5$ and R$^7$ are as hereinbefore defined) with a reactive acid halide, e.g. phosphorus pentachloride.

(b) by the reaction of an amine of formula XII with a compound of formula XXV in the presence of phosphorus oxychloride in a suitable solvent, e.g. dimethylformamide, at a temperature between 0° C and the reflux temperature of the reaction mixture.

(c) by the reaction of a compound of the general formula:

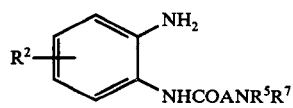   XXVI (wherein A, R$^2$, R$^5$ and R$^7$ are as hereinbefore defined) with a compound of formula VIII by methods hereinbefore described for the preparation of compounds of formula IV from amines of formula IX.

Compounds of formula XXVI may be prepared by the reduction of compounds of formula:

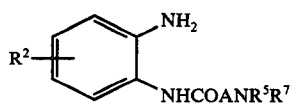   XXVII (wherein A, R$^2$, R$^5$ and R$^7$ are as hereinbefore defined) by known methods for the reduction of aromatic nitro groups to amino groups, for example by the use of ferrous chloride and reduced iron powder.

Compounds of formula XXVII may be prepared by the reaction of compounds of formula XXI with compounds of formula XXIV or XXV by methods hereinbefore described for the preparation of compounds of formula XVIII.

Compounds of formula XII may be prepared by the reaction of compounds of formula XXI with an isothiocyanate of formula VIII, preferably in the reaction conditions hereinbefore described for the reaction between compounds of formulae VIII and IX, and reduction of the nitro group in the resulting compound of the general formula:

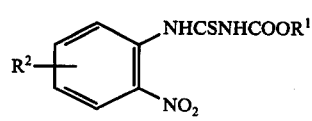   XXVIII (wherein R$^1$ and R$^2$ are as hereinbefore defined) to a primary amino group by known methods for the reduction of aromatic nitro groups to amino groups, for example as hereinbefore described for the reduction of compounds of general formula XIX.

By the term 'known methods' as used in the present specification is meant methods heretofore used or described in the chemical literature.

The following Examples illustrate the preparation of the new benzene derivatives according to the present invention.

The Reference Examples following thereafter illustrate the preparation of starting materials used in the Examples.

EXAMPLE 1

Compound A (Hydrochloride)

A stirred solution of 4-(3-methoxycarbonyl-2-thioureido)-3-(2-dimethylaminoacetamido)diphenyl thioether (20.0 g) in dry dimethylformamide (100 ml) was cooled to 10° C and treated with chloroacetyl chloride (6.0 g), dropwise. The mixture was stirred at 10° C for 1 hour and then allowed to stand overnight at room temperature. The mixture was diluted with acetone (300 ml), cooled in an ice bath, and the solid was filtered off and washed with acetone to give 3-[2-(2-dimethylaminoacetamido)-4-phenylthiophenyl]-2-methoxycarbonyliminothiazolidin-4-one hydrochloride (16.0 g), m.p. 205°–207° C (with decomposition).

EXAMPLE 2

Compound A

3-[2-(2-Dimethylaminoacetamido)-4-phenylthiophenyl]-2-methoxycarbonyliminothiazolidin-4-one hydrochloride (16.0 g; prepared as described in Example 1) was suspended in a mixture of water (150 ml) and chloroform (150 ml). Anhydrous sodium carbonate (1.75 g) was added, and the mixture was shaken vigorously. The chloroform layer was separated and the aqueous layer was extracted with a further quantity of chloroform (2 × 50 ml). The combined chloroform layers were dried over magnesium sulphate and evaporated. The residual solid obtained was crystallised from ethanol, with the aid of decolourising charcoal, to give 3-[2-(2-dimethylaminoacetamido)-4-phenylthiophenyl]-

2-methoxycarboniliminothiazolidin-4-one (13.1 g), m.p. 124°–126° C.

EXAMPLE 3

Compounds B, C, D, E and F (hydrochlorides)

By proceeding in a similar manner to that hereinbefore described in Example 1 but replacing the 4-(3-methoxycarbonyl-2-thioureido)-3-(2-dimethylaminoacetamido)diphenyl thioether used as starting material by the appropriate quantities of:

4-allylthio-1-(3-methoxycarbonyl-2-thioureido)-2-(2-dimethylaminoacetamido)benzene,
4-ethylthio-1-(3-methoxycarbonyl-2-thioureido)-2-(2-dimethylaminoacetamido)benzene,
3-(2-diethylaminoacetamido)-4-(3-methoxycarbonyl-2-thioureido)-diphenyl thioether.
3-(3-methoxycarbonyl-2-thioureido)-4-(2-dimethylaminoacetamido)diphenyl thioether, and
4-cyclohexylmethylthio-1-(3-methoxycarbonyl-2-thioureido)-2-(2-dimethylaminoacetamido)benzene, respectively, there were prepared:

3-[4-allylthio-2-(2-dimethylaminoacetamido)phenyl]-2-methoxycarbonyliminothiazolidin-4-one hydrochloride, m.p. 200°–202° C (with decomposition),
3-[4-ethylthio-2-(2-dimethylaminoacetamido)phenyl]-2-methoxycarbonyliminothiazolidin-4-one hydrochloride, m.p. 204°–205° C (with decomposition),
3-[2-(2-diethylaminoacetamido)-4-phenylthiophenyl]-2-methoxycarbonyliminothiazolidin-4-one hydrochloride, m.p. 200° C (with decomposition),
3-[2-(2-dimethylaminoacetamido)-5-phenylthiophenyl]-2-methoxycarbonyliminothiazolidin-4-one hydrochloride, m.p. 190°–192° C (with decomposition), and
3-[4-cyclohexylmethylthio-2-(2-dimethylaminoacetamido)phenyl]-2-methoxycarbonyliminothiazolidin-4-one hydrochloride, m.p. 196°–200° C (with decomposition).

EXAMPLE 4

Compounds B, C, D, E and F

By proceeding in a similar manner to that hereinbefore described in Example 2 but replacing the 3-[2-(2-dimethylaminoacetamido)-4-phenylthiophenyl]-2-methoxycarbonyliminothiazolidin-4-one hydrochloride used as starting material by the appropriate quantities of:

3-[4-allylthio-2-(2-dimethylaminoacetamido)phenyl]-2-methoxycarbonyliminothiazolidin-4-one hydrochloride,
3-[4-ethylthio-2-(2-dimethylaminoacetamido)phenyl]-2-methoxycarbonyliminothiazolidin-4-one hydrochloride,
3-[2-(2-diethylaminoacetamido)-4-phenylthiophenyl]-2-methoxycarbonyliminothiazolidin-4-one hydrochloride,
3-[2-(2-dimethylaminoacetamido)-5-phenylthiophenyl]-2-methoxycarbonyliminothiazolidin-4-one hydrochloride, and
3-[4-cyclohexylmethylthio-2-(2-dimethylaminoacetamido)phenyl]-2-methoxycarbonyliminothiazolidin-4-one hydrochloride, respectively (all prepared as described in Example 3), there were prepared:

3-[4-allylthio-2-(2-dimethylaminoacetamido)phenyl]-2-methoxycarbonyliminothiazolidin-4-one, m.p. 131°–133° C,
3-[4-ethylthio-2-(2-dimethylaminoacetamido)phenyl]-2-methoxycarbonyliminothiazolidin-4-one, m.p. 171°–173° C,
3-[2-(2-diethylaminoacetamido)-4-phenylthiophenyl]-2-methoxycarbonyliminothiazolidin-4-one, m.p. 119°–121° C,
3-[2-(2-dimethylaminoacetamido)-5-phenylthiophenyl]-2-methoxycarbonyliminothiazolidin-4-one, m.p. 150°–152° C, and
3-[4-cyclohexylmethylthio-2-(2-dimethylaminoacetamido)phenyl]-2-methoxycarbonyliminothiazolidin-4-one, m.p. 145°–147° C.

EXAMPLE 5

Compounds G and H (and their hydrochlorides)

A stirred solution of 4-n-butylthio-1-(3-methoxycarbonyl-2-thioureido)-2-(2-dimethylaminoacetamido)benzene (17.9 g) in dry dimethylformamide (80 ml) was treated dropwise with chloroacetyl chloride (5.7 g) at 15° C. The stirring was continued for 6 hours and the mixture was then allowed to stand overnight. It was then diluted with acetone (150 ml). The solid (crude hydrochloride of compound (G) was filtered off, washed with acetone, and dried.

The solid was then suspended in methanol (100 ml) and the suspension was treated with triethylamine (5.0 g) with stirring. A solution was formed from which a solid (5a) soon precipitated. The solid (5a) was filtered off and the filtrate was then diluted with an excess of diethyl ether. The resulting precipitate of triethylamine hydrochloride was filtered off. The filtrate was evaporated and the resulting oil was triturated with isopropanol to give a solid (5b). The solid (5b) was filtered off and was mixed with solid (5a). This mixture was recrystallised from ethanol, to give 3-[4-n-butylthio-2-(2-dimethylaminoacetamido)phenyl]-2-methoxycarbonyliminothiazolidin-4-one, m.p. 116°–118° C.

By proceeding in a similar manner but replacing the 4-n-butylthio-1-(3-methoxycarbonyl-2-thioureido)-2-(2-dimethylaminoacetamido)benzene used as starting material by the appropriate quantity of 4-benzylthio-1-(3-methoxycarbonyl-2-thioureido)-2-(2-dimethylaminoacetamido)benzene, there was prepared 3-[4-benzylthio-2-(2-dimethylaminoacetamido)phenyl]-2-methoxycarbonyliminothiazolidin-4-one, m.p. 154°–158° C (with decomposition).

EXAMPLE 6

Compounds I, J, K and L (and their hydrochlorides)

A solution of 4-cyclopentylthio-2-(2-dimethylaminoacetamido)-1-(3-methoxycarbonyl-2-thioureido)benzene (15.5 g) in dry dimethylformamide (105 ml) was cooled to 10° C and treated dropwise with stirring with chloroacetyl chloride (4.41 g). The mixture was stirred for 5 hours and the solid which precipitated (crude hydrochloride of compound I) was filtered off, washed with diethyl ether, and dried. The solid was then dissolved in water (200 ml) and the solution was filtered to remove some insoluble material. The filtrate was adjusted to pH 9 by treatment with saturated aqueous sodium carbonate solution and was then extracted with chloroform (4 × 200 ml). The combined extracts were dried over sodium sulphate and evaporated. The residue was recrystallised from ethanol to give 3-[4-cyclopentylthio-2-(2-dimethylaminoacetamido)-phenyl]-2-methoxycarbonyliminothiazolidin-4-one, m.p. 167°–169° C.

By proceeding in a similar manner but replacing the 4-cyclopentylthio-2-(2-dimethylaminoacetamido)-1-(3-methoxycarbonyl-2-thioureido)benzene used as starting material by the appropriate quantities of:

2-(2-dimethylaminoacetamido)-1-(3-methoxycarbonyl-2-thioureido)-4-n-pentylthiobenzene, 2-(2-dimethylaminoacetamido)-1-(3-methoxycarbonyl-2-thioureido)-4-n-propylthiobenzene, and 3-(3-dimethylaminopropionamido)-4-(3-methoxycarbonyl-1-thioureido)-diphenyl thioether, respectively, there were prepared:

3-[2-(2-dimethylaminoacetamido)-4-n-pentylthio-phenyl]-2-methoxycarbonyliminothiazolidin-4-one, m.p. 126°–128° C, 3-[2-(2-dimethylaminoacetamido)-4-n-propylthio-phenyl]-2-methoxycarbonyliminothiazolidin-4-one, m.p. 122°–124° C, and 3-[2-(3-dimethylaminopropionamido)-4-phenylthio-phenyl]-2-methoxycarbonyliminothiazolidin-4-one, m.p. 91°–93° C.

REFERENCE EXAMPLE 1

Starting material for Compound A (a) Thiophenol (44 g) was added, over a period of 5 minutes and under an atmosphere of dry nitrogen, to a suspension of 5-chloro-2-nitro-aniline (66.5 g; prepared according to Fuson et al., J. Org. Chem., 12, 799–806, 1947) and anhydrous potassium carbonate (60.6 g) in dimethylformamide (200 ml). The reaction mixture was heated under reflux for 8 hours and then cooled. Water (200 ml) was added dropwise whilst maintaining the temperature at 5°–10° C. The precipitated solid was filtered off, washed well with water and recrystallised from isopropanol, to give 3-amino-4-nitro-diphenyl thioether (83 g), m.p. 117°–118° C, in the form of a pale brown solid.

(b) Chloroacetyl chloride (6.2 g) was added to a stirred solution of 3-amino-4-nitro-diphenyl thioether (12.3 g) in dry toluene (50 ml). The solution was heated at reflux for 1 hour. The hot solution was added to petrol (80 ml; b.p. 60°–80° C), whereupon 3-(2-chloroacetamido)-4-nitrodiphenyl thioether crystallised in the form of a yellow solid (15.8 g), m.p. 152°–154° C.

(c) A solution of dimethylamine in ethanol (33% w/v; 60 ml) was added to a suspension of 3-(2-chloroacetamido)-4-nitrodiphenyl thioether (15.5 g) in ethanol (140 ml). The suspension was stirred and heated at reflux for one hour. The cooled solution was concentrated in vacuo to give a yellow solid. The solid was washed with ice-cold ethanol (10 ml) and then suspended in water (100 ml). The solid was filtered off, washed with water and dried at 80° C, to give 3-(2-dimethylaminoacetamido)-4-nitrodiphenyl thioether (14.9 g).

(d) To a solution of 3-(2-dimethylaminoacetamido)-4-nitrodiphenyl thioether (14.9 g) in ethyl acetate (200 ml), there was added palladium on charcoal catalyst (6 g; 5% Pd w/w). The suspension was shaken in an atmosphere of hydrogen at atmospheric pressure and room temperature.

After 90 minutes 3.1 liters of hydrogen had been absorbed. The solution was filtered and concentrated in vacuo to give 4-amino-3-(2-dimethylaminoacetamido)-diphenyl thioether (12.9 g) in the form of a white solid, m.p. 131°–133° C.

(e) A solution of 4-amino-3-(2-dimethylaminoacetamido)diphenyl thioether (6.4 g) in dry acetone (100 ml) was stirred during the dropwise addition of methoxycarbonyl isothiocyanate (2.7 g), the temperature being maintained between 15° C and 20° C by external cooling and afterwards at the same temperature for a further 20 minutes. The solution was concentrated in vacuo to form a yellow oil which was triturated with diethyl ether. The solid product was recrystallised from isopropanol to give 4-(3-methoxycarbonyl-2-thioureido)-3-(2-dimethylaminoacetamido)diphenyl thioether (4.0 g), in the form of a pale buff solid, m.p. 143°–144° C (with decomposition).

REFERENCE EXAMPLE 2

Starting materials for Compounds, B, C, F, G, H, I, J and K (a) A stirred mixture of o-nitroaniline (82.5 g), dry sodium thiocyanate (180 g) and acetic acid (1 liter) was treated at 11°–12° C with a solution of bromine (96.5 g) in acetic acid (100 ml). The stirring was continued for a further hour at 11°–12° C and the mixture was then allowed to warm to 15° C and poured into water (3.5 liters). The yellow solid was filtered off, washed with water, and dissolved in acetone (1 liter). The solution was filtered and the filtrate was evaporated to give 2-nitro-4-thiocyanatoaniline (107 g), m.p. 110°–112° C.

(b) 2-Nitro-4-thiocyanatoaniline (17.55 g) was added portionwise to a stirred solution of potassium hydroxide (13.4 g) in ethanol (210 ml), keeping the temperature below 20° C. After 5 minutes, ethyl iodide (14.4 g) was added during five minutes. The stirring was continued for a further hour and the mixture was allowed to stand overnight. The mixture was then poured into water (1100 ml) and extracted with chloroform (3 × 300 ml). The chloroform layers were combined, washed with water (500 ml), dried over magnesium sulphate, and evaporated to give 1-amino-4-ethylthio-2-nitrobenzene (17.0 g), in the form of a red oil.

By proceeding in a similar manner but replacing the ethyl iodide used as a starting material by the appropriate quantities of allyl bromide, n-butyl iodide, n-pentyl bromide, n-propyl bromide, cyclopentyl bromide, cyclohexylmethyl bromide and benzyl bromide, respectively, there were prepared:

4-allylthio-1-amino-2-nitrobenzene, in the form of a red oil, 1-amino-4-n-butylthio-2-nitrobenzene, in the form of a red oil, 1-amino-2-nitro-4-n-pentylthiobenzene, in the form of a red oil, 1-amino-2-nitro-4-n-propylthiobenzene, in the form of a red oil, 1-amino-4-cyclopentylthio-2-nitrobenzne, in the form of a brown oil, 1-amino-4-cyclohexylmethylthio-2-nitrobenzene, m.p. 77°–80° C, and 1-amino-4-benzylthio-2-nitrobenzene, m.p. 97°–99° C.

(c) A mixture of dry potassium thiocyanate (25.65 g) and acetonitrile (320 ml) was cooled to 10° C and treated during 5 minutes with methyl chloroformate (25.0 g). The mixture was stirred at room temperature for 2 hours. 1-Amino-4-ethylthio-2-nitrobenzene (22.45 g) was then added to the mixture at 10°–15° C. The suspension was stirred for 3 hours at room temperature and allowed to stand overnight. It was then poured into water (1.6 liters) and the solid which precipitated was filtered off, washed with water and recrystallised from a mixture of methanol and ethanol, to give 4-ethylthio-1-(3-methoxycarbonyl-2-thioureido)-2-nitrobenzene (14.0 g), m.p. 152° C.

By proceeding in a similar manner but replacing the 1-amino-4-ethylthio-2-nitrobenzene used as starting material by the appropriate quantities of 4-allylthio-1-amino-2-nitrobenzene,
1-amino-4-n-butylthio-2-nitrobenzene,
1-amino-2-nitro-4-n-pentylthiobenzene,
1-amino-2-nitro-4-n-propylthiobenzene,
1-amino-4-cyclopentylthio-2-nitrobenzene,
1-amino-4-cyclohexylmethylthio-2-nitrobenzene, and
1-amino-4-benzylthio-2-nitrobenzene, respectively, there were prepared:
4-allylthio-1-(3-methoxycarbonyl-2-thiouredio)-2-nitrobenzene, m.p. 121°–123° C,
4-n-butylthio-1-(3-methoxycarbonyl-2-thiouredio)-2-nitrobenzene, m.p. 129°–131° C,
1-(3-methoxycarbonyl-2-thioureido)-2-nitro-4-n-pentylthiobenzene, m.p. 117°–119° C,
1-(3-methoxycarbonyl-2-thioureido)-2-nitro-4-n-propylthiobenzene, m.p. 119°–120° C (with decomposition),
4-cyclopentylthio-1-(3-methoxycarbonyl-2-thioureido)-2-nitrobenzene, m.p. 123° C,
4-cyclohexylmethylthio-1-(3-methoxycarbonyl-2-thioureido)-2-nitrobenzene, m.p. 121°–123° C, and
4-benzylthio-1-(3-methoxycarbonyl-2-thioureido)-2-nitrobenzene, m.p. 172°–174° C (with decomposition).

(d) A mixture of 4-ethylthio-1-(3-methoxycarbonyl-2-thioureido)-2-nitrobenzene (14.0 g), ferrous chloride tetrahydrate (3.04 g), methanol (235 ml) and water (50 ml) was heated to reflux and treated with reduced iron powder (15.5 g) portionwise during 5 minutes. The mixture was heated to reflux with stirring for one hour. Methanol (250 ml) was added and the mixture was again heated to reflux. The hot mixture was filtered and the filtrate was allowed to cool to room temperature. The solid which crystallised on cooling was filtered off to give 2-amino-4-ethylthio-1-(3-methoxycarbonyl-2-thioureido)benzene (7.5 g), m.p. 168° C.

By proceeding in a similar manner but replacing the 4-ethylthio-1-(3-methoxycarbonyl-2-thioureido)-2-nitrobenzene used as a starting material by the appropriate quantities of 4-allylthio-1-(3-methoxycarbonyl-2-thioureido)-2-nitrobenzene,
4-n-butylthio-1-(3-methoxycarbonyl-2-thioureido)-2-nitrobenzene,
1-(3-methoxycarbonyl-2-thioureido)-2-nitro-4-n-pentylthiobenzene,
1-(3-methoxycarbonyl-2-thioureido)-2-nitro-4-n-propylthiobenzene,
4-cyclopentylthio-1-(3-methoxycarbonyl-2-thioureido)-2-nitrobenzene,
4-cyclohexylmethylthio-1-(3-methoxycarbonyl-2-thioureido)-2-nitrobenzene, and
4-benzylthio-1-(3-methoxycarbonyl-2-thioureido)-2-nitrobenzene, respectively, there were prepared:
4-allylthio-2-amino-1-(3-methoxycarbonyl-2-thioureido)benzene, m.p. 164°–165° C, (with decomposition),
2-amino-4-n-butylthio-1-(3-methoxycarbonyl-2-thioureido)benzene, m.p. 164°–165° C (with decomposition),
2-amino-1-(3-methoxycarbonyl-2-thioureido)-4-n-pentylthiobenzene, m.p. 153°–154° C (with decomposition),
2-amino-1-(3-methoxycarbonyl-2-thioureido)-4-n-propylthiobenzene, m.p. 171°–173° C (with decomposition),
2-amino-4-cyclopentylthio-1-(3-methoxycarbonyl-2-thioureido)benzene, m.p. 169°–172° C,
2-amino-4-cyclohexylmethylthio-1-(3-methoxycarbonyl-2-thioureido)benzene m.p. 182°–184° C (with decomposition), and
2-amino-4-benzylthio-1-(3-methoxycarbonyl-2-thioureido)benzene, m.p. 191°–193° C.

(e) A stirred solution of 2-amino-4-ethylthio-1-(3-methoxycarbonyl-2-thioureido)benzene (8.35 g) in dry dimethylformamide (60 ml) was treated at room temperature with N,N-dimethylglycyl chloride hydrochloride (5.53 g). The mixture was heated to 40°–50° C for 45 minutes, then cooled, and diluted with diethyl ether (900 ml). An oil precipitated which crystallised on standing. This solid was filtered off, washed with diethyl ether (100 ml), and suspended in a mixture of chloroform (100 ml) and water (100 ml). Sodium carbonate (3.5 g) was added and the mixture was stirred for 20 minutes. The chloroform layer was separated and the aqueous layer was extracted twice with chloroform (2 × 50 ml). The organic layers were combined, dried over magnesium sulphate and evaporated to dryness. The residual solid was recrystallised from isopropanol to give 4-ethylthio-1-(3-methoxycarbonyl-2-thioureido)-2-(2-dimethylaminoacetamido)benzene (8.5 g), m.p. 142° C (with decomposition).

By proceeding in a similar manner but replacing the 2-amino-4-ethylthio-1-(3-methoxycarbonyl-2-thioureido)benzene used as starting material by the appropriate quantities of 4-allylthio-2-amino-1-(3-methoxycarbonyl-2-thioureido)benzene,
2-amino-4-n-butylthio-1-(3-methoxycarbonyl-2-thioureido)benzene,
2-amino-1-(3-methoxycarbonyl-2-thioureido)-4-n-pentylthiobenzene,
2-amino-1-(3-methoxycarbonyl-2-thioureido)-4-n-propylthiobenzene,
2-amino-4-cyclopentylthio-1-(3-methoxycarbonyl-2-thioureido)benzene,
2-amino-4-cyclohexylmethylthio-1-(3-methoxycarbonyl-2-thioureido)benzene, and
2-amino-4-benzylthio-1-(3-methoxycarbonyl-2-thioureido)benzene, respectively, there were prepared:
4-allylthio-1-(3-methoxycarbonyl-2-thioureido)-2-(2-dimethylaminoacetamido)benzene, m.p. 133°–134° C (with decomposition),
4-n-butylthio-1-(3-methoxycarbonyl-2-thioureido)-2-(2-dimethylaminoacetamido)benzene, m.p. 104°–106° C,
1-(3-methoxycarbonyl-2-thioureido)-2-(2-dimethylaminoacetamido)-4-n-pentylthiobenzene, m.p. 96°–98° C (with decomposition), 1-(3-methoxycarbonyl-2-thioureido)-2-(2-dimethylaminoacetamido)-4-n-propylthiobenzene, m.p. 108°–110° C (with decomposition), 4-cyclopentylthio-1-(3-methoxycarbonyl-2-thioureido)-2-(2-dimethylaminoacetamido)benzene, m.p. 126°–130° C (with decomposition), 4-cyclohexylmethylthio-1-(3-methoxycarbonyl-2-thioureido)-2-(2-dimethylaminoacetamido)benzene, m.p. 117°–119° C (with decomposition), and, 4-benzylthio-1-(3-methoxycarbonyl-2-thioureido)-2-(2-dimethylaminoacetamido)benzene, m.p. 115°–116° C.

REFERENCE EXAMPLE 3

Starting material for Compound E (a) Methoxycarbonyl isothiocyanate (12 g) was added dropwise during 5 minutes to a stirred solution of 3-amino-4-nitrodiphenyl thioether (prepared as hereinbefore described in Reference Example 1; 12.3 g) in acetonitrile (90 ml). The reaction temperature was maintained at 15°–20° C during the addition by external cooling. The mixture was then warmed to 40°–45° C and stirred for a further 5 hours, during which time a yellow solid separated. The reaction mixture was cooled in ice and filtered. The residue was washed with diethyl ether and dried to give 3-(3-methoxycarbonyl-2-thioureido)-4-nitrodiphenyl thioether (12.9 g), m.p. 144°–145° C (with decomposition).

(b) Reduced iron powder (11.1 g) was added portionwise, during 5 minutes, to a rapidly stirred mixture of 3-(3-methoxycarbonyl-2-thioureido)-4-nitrodiphenyl thioether (12.1 g) and ferrous chloride tetrahydrate (2.2 g) in methanol (167 ml) and water (37 ml) heated at reflux. After 90 minutes the black suspension was diluted with methanol (150 ml), filtered hot through a Hyflo bed and the Hyflo bed was washed twice with hot methanol (2 × 50 ml). The combined solution was re-heated, treated with decolourising charcoal, filtered hot and then concentrated under reduced pressure to about one half its volume. The off-white solid which separated was filtered after cooling, sucked dry on the filter and recrystallised from a mixture of methanol (450 ml) and water (250 ml) to give 4-amino-3-(3-methoxycarbonyl-2-thioureido)diphenyl thioether (8.1 g), m.p. 164°–165° C.

(c) To a stirred solution of 4-amino-3-(3-methoxycarbonyl-2-thioureido)diphenyl thioether (7.9 g) in dimethylformamide (50 ml) there was added during 5 minutes N,N-dimethylglycyl chloride hydrochloride (3.8 g). The reaction temperature rose to 37° C during the addition and a white solid began to separate. The reaction mixture was then stirred and heated at 40°–45° C for 75 minutes, cooled and diluted with acetone (150 ml). The solid was filtered off, washed with acetone and sucked dry. This solid was dissolved in a boiling mixture of methanol (100 ml) and water (10 ml), and the solution was treated with decolourising charcoal, filtered hot and allowed to crystallise to give 3-(3-methoxycarbonyl-2-thioureido)-4-(2-dimethylaminoacetamido)diphenyl thioether hydrochloride (5.25 g), in the form of a white crystalline solid, m.p. 192°–193° C (with decomposition).

(d) 3-(3-Methoxycarbonyl-2-thioureido)-4-(2-dimethylaminoacetamido)diphenyl thioether hydrochloride (18.9 g) was suspended in water and the suspension was treated with aqueous sodium carbonate solution (2N; 50 ml) and then extracted with chloroform. The extract was dried over magnesium sulphate and evaporated and the residual solid was recrystallised from ethanol to give 3-(3-methoxycarbonyl-2-thioureido)-4-(2-dimethylaminoacetamido)diphenyl thioether (9.9 g), m.p. 149°–150° C (with decomposition).

REFERENCE EXAMPLE 4

Starting materials for compounds D and L (a) A solution of 3-amino-4-nitrodiphenyl thioether (prepared as hereinbefore described in Reference Example 1; 40 g) in toluene (170 ml) at 45° C was treated dropwise, with stirring, with 3-chloropropionyl chloride (24.8 g) during 5 minutes. An exothermic reaction occurred and, at the end of the addition, the mixture was heated at reflux for one hour. It was then poured into petroleum ether (b.p. 60°–80° C, 400 ml) and allowed to cool. The precipitate which formed was filtered off, washed with petroleum ether (b.p. 60°–80° C; 4 × 200 ml) and dried to give 3-(3-chloropropionamido)-4-nitrodiphenyl thioether (50.1 g), m.p. 143°–145° C.

(b) A suspension of 3-(3-chloropropionamido)-4-nitrodiphenyl thioether (50 g) in dry toluene (220 ml) was mixed with a solution of dimethylamine in toluene (110 g; 25% w/w) and the mixture was heated in a closed vessel on the steam bath for 24 hours. The mixture was then cooled in an ice-bath, filtered and evaporated. The resulting oil was triturated with petroleum ether (b.p. 60°–80° C) to obtain a solid, which was filtered off and recrystallised from a mixture of petroleum ether (b.p. 60°–80° C) and isopropanol to give 3-(3-dimethylaminopropionamido)-4-nitrodiphenyl thioether (33.5 g), m.p. 67°–69° C.

By proceeding in a similar manner but replacing the 3-(3-chloropropionamido)-4-nitrodiphenyl thioether and the dimethylamine by the appropriate quantities of 3-(2-chloroacetamido)-4-nitrodiphenyl thioether (prepared as described in Reference Example 1) and diethylamine, respectively, there was prepared 3-(2-diethylaminoacetamido)-4-nitrodiphenyl thioether, m.p. 57°–58° C.

(c) A solution of 3-(3-dimethylaminopropionamido)-4-nitrodiphenyl thioether (33.0 g) in ethyl acetate (400 ml) was mixed with a catalyst of palladium or charcoal (11 g; 5%Pd w/w) and the mixture was shaken in an atmosphere of hydrogen at room temperature and atmospheric pressure, until 6.4 liters had been absorbed. The catalyst was filtered off and washed with boiling ethyl acetate (2 × 300 ml) and the combined filtrate and washings were evaporated to give a solid, which was recrystallised from isopropanol to give 4-amino-3-(3-dimethylaminopropionamido)diphenyl thioether (22.6 g), m.p. 129°–131° C.

By proceeding in a similar manner but replacing the 3-(3-dimethylaminopropionamido)-4-nitrodiphenyl thioether used as starting material by the appropriate quantity of 3-(2-diethylaminoacetamido)-4-nitrodiphenyl thioether, there was prepared 4-amino-3-(2-diethylaminoacetamido)diphenyl thioether, m.p. 76°–78° C.

(d) Methyl chloroformate (24.6 g) was added to a suspension of potassium thiocyanate (25.2 g) in ethyl acetate (180 ml) and the mixture was heated, with stirring, at 60°–70° C for 3 hours. The mixture was then filtered and the filtrate was added dropwise during 10 minutes to a solution of 4-amino-3-(3-dimethylaminopropionamido)diphenyl thioether (22.0 g) in glacial acetic acid (200 ml). This mixture was stirred overnight at room temperature and then poured into cold water (1200 ml). The mixture was adjusted to pH 9 by treatment with aqueous sodium carbonate solution and was then extracted with ethyl acetate (1 × 1100 ml and 2 × 500 ml). The combined extracts were dried over sodium sulphate and evaporated, to give a solid which was recrystallised from isopropanol to give 4-(3-methoxycarbonyl-2-thioureido)-3-(3-dimethylaminopropionamido)diphenyl thioether (22.5 g), m.p. 148°–149° C.

By proceeding in a similar manner but replacing the 4-amino-3-(3-dimethylaminopropionamido)diphenyl thioether by the appropriate quantity of 4-amino-3-(2-diethylaminoacetamido)diphenyl thioether, there was prepared 3-(2-diethylaminoacetamido)-4-(3-methoxycarbonyl-2-thioureido)diphenyl thioether, m.p. 136°–137° C (with decomposition).

According to a feature of the present invention, there is provided a method for the treatment of helminth infections in man and domestic animals, for example cattle, sheep, pigs, goats, poultry and equines, for example infections of the gastro-intestinal tract caused by parasitic nematode worms, for example members of the family Trichostrongylidae, and infections by parasitic trematodes of the genus Fasciola (e.g. *Fasciola hepatica*) in domestic animals, which comprises the administration of an anthelmintically effective amount of one or more compounds of general formula I.

The quantities of the compounds of formula I administered in the treatment of helminthiasis will vary with the species of animal treated, the nature and severity of the infection, the length of treatment and the method of administration. In general, the compounds are effective in treating helminthiasis when administered to domestic animals in dosages which may be as low as 1 mg/kg of animal body weight but which are preferably from about 4 mg/kg to about 50 mg/kg of animal body weight. Higher doses up to 250 mg/kg of animal body weight may, however, be used. When administered by continuous medication, doses as low as 0.1 mg/kg of animal body weight may be suitable.

The quantities referred to above of the compound of general formula I may be administered on one or more occasions or divided into a number of smaller doses and administered over a period.

The compounds of general formula I are conveniently administered as anthelmintic agents in the form of compositions in a unit dosage form, and the present invention includes within its scope therapeutically-useful, more especially veterinary, compositions which comprise, as active ingredient, at least one benzene derivative of formula I in associaton with a significant amount of one or more compatible and pharmaceutically-acceptable carriers or adjuvants. The invention includes especially such compositions made up for oral administration, for example a tablet, pill, capsule or bolus, or more particularly, a paste, gel or drench.

Solid compositions for oral administration include comprressed tablets, pills, boluses and granules, which may optionally be coated with a pharmaceutically acceptable alkali-stable or acid-stable material (e.g. an enteric coating) and dispersible powders. In such solid compositions one or more of the active compounds is or are admixed with at least one inert diluent such as potato starch, alginic acid, sucrose, lactose, or a resin. The compositions may also comprise, as is normal practice, additional substances other than inert diluents, e.g. lubricating agents such as magnesium stearate. Semi-solid compositions for oral administration include pastes and gels containing the active substance and a suitable inert diluent such as polyethylene glycol (6000). Liquid compositions for oral administration include pharmaceutically acceptable emulsions, solutions, suspensions, syrups and elixirs containing inert diluents commonly used in the art, such as water and liquid paraffin. Besides inert diluents such compositions may also comprise compatible adjuvants such as wetting, suspending and emulsifying agents and stabilising, thickening, perfuming, sweetening and flavouring agents. The compositions according to the invention for oral administration also include capsules of absorbable material such as gelatin containing one or more of the active substances with or without the addition of diluents or excipients.

Preparations according to the invention for parenteral administration include sterile aqueous, aqueous-organic and organic solutions, suspensions and emulsions. Examples of organic solvents or suspending media are propylene glycol, polyethylene glycol, vegetable oils such as olive oil and injectable organic esters such as ethyl oleate. These compositions may also contain adjuvants such as stabilising, preserving, wetting, emulsifying and dispersing agents. They may be sterilised, for example, by filtration through a bacteria-retaining filter, by incorporation in the compositions of sterilising agents, or by heating. They may also be manufactured in the form of sterile solid compositions, which can be dissolved in sterile water or some other sterile injectable medium immediately before use.

The percentage of the benzene derivatives of formula I in the above compositions may be varied, it being necessary that it should constitute a proportion such that a suitable dosage for the therapeutic effect desired shall be obtained. In general, compositions containing from about 5% to about 90% by weight of active ingredient are satisfactory.

The compounds of general formula I may also be conveniently administered as anthelmintics by dermal application and absorption through the skin of the animal and the present invention includes within its scope liquid therapeutically-useful, more especially veterinary, compositions suitable for dermal administration which comprise, as active ingredient, at least one benzene derivative of formula I in association with a significant amount of a liquid pharmaceutically-acceptable carrier suitable for dermal application. Compositions for dermal administration according to the present invention preferably comprise a solution of at least one benzene derivative of general formula I in a liquid pharmaceutically-acceptable solvent, for example, a hydrocarbon, e.g. xylene, toluene, benzene or a mixture of aromatic hydrocarbons whose boiling point is between 130° C and 250° C, e.g. between 180° C and 220° C, or paraffins containing from 6 to 20 carbon atoms, halogenated hydrocarbons, e.g. carbon tetrachloride, ketones, e.g. cyclohexanone or butanone, esters, e.g. ethyl acetate, ethyl benzoate or glyceryl triacetate, ethers, e.g. diisopropyl ether or tetrahydrofuran, alcohols, e.g. alkanols containing from 2 to 8 carbon atoms (e.g. butanol, isopropanol or amyl alcohol) or glycols (e.g. propylene glycol), amides, e.g. lower alkyl amides (e.g. dimethylformamide), sulphones, e.g. lower dialkyl sulphones (e.g. dimethyl sulphone) or sulpholane, or sulphoxides, e.g. lower dialkyl sulphoxides (e.g. dimethyl sulphoxide or mixtures of such solvents. Preferred carriers for compositions suitable for dermal application are amyl alcohol and dimethyl sulphoxide and mixtures thereof. Liquid compositions suitable for dermal application preferably contain a thickening agent in order to reduce run-off of the liquid composition from the skin of the animal, thereby facilitating absorption of the active ingredient through the skin of the animal. Suitable thickening agents are, for example, soaps, fats and waxes, e.g. lanolin, mineral or vegetable oils and polymers, e.g. polyisobutylene. Liquid compositions suitable for dermal application may also contain systemic insecticides known to be suitable for dermal administration to animals, e.g. phosalone, and bitter aloes, which inhibits licking of the treated skin by other animals. The liquid compositions for dermal administration may be applied to the skin of the animal by conventional techniques, e.g. dipping, spraying and pouring over the back of the animal. The percentage of the benzene derivative of formula I in the liquid compositions suitable for dermal application may be varied, it being necessary that it should constitute a proportion such that a suitable dosage for the therapeutic effect desired is obtained. preferably, the liquid compositions suitable for dermal administration contain from 1% to 10% weight/volume of the benzene derivative of formula I, from 45% to 95% volume/volume of liquid pharmaceutically-acceptable carrier and from 5% to 50% weight/volume of thickening agent and/or systemic insecticide.

For therapeutic purposes, particularly when continuous administration over a period is desired, the compounds of general formula I may be administered dissolved in, dispersed in, or mixed with, animal feedstuffs, drinking water and other liquids normally consumed by the animals, or in compositions containing the benzene derivatives dispersed in or mixed with any other suitable inert physiologically innocuous carrier or diluent which is orally administrable. By the term 'inert physiologically innocuous carrier or diluent' is meant a carrier or diluent which is substantially non-reactive with the active ingredient and is not harmful to the animals on oral administration. Such compositions may be administered in the form of powders, pellets, feed blocks, licks, solutions, suspensions and emulsions, to the animals to supply the desired dosage of the benzene derivatives or used as concentrates or supplements to be diluted with additional carrier, feedstuff, drinking water or other liquids normally consumed by the animals, before administration. Suitable inert physiologically innocuous carriers or diluents include cereals, e.g. wheat flour or meal, maize gluten, lactose, glucose, sucrose, molasses, talc, kaolin, calcium phosphate, potassium sulphate, sodium chloride, urea and diatomaceous earths such as kieselguhr. Concentrates or supplements intended for incorporation into drinking water or other liquids normally consumed by the animals to give solutions, emulsions or stable suspensions, may also comprise the active ingredient in association with a surface-active wetting, dispersing or emulsifying agent such as Teepol, polyoxyethylene(20)sorbitan mono-oleate or the condensation product of β-naphthalenesulphonic acid with formaldehyde, with or without a physiologically innocuous, preferably water-soluble, carrier or diluent, for example, sucrose, glucose or an inorganic salt such as potassium sulphate, or concentrates or supplements in the form of stable dispersions or solutions obtained by mixing the aforesaid concentrates or supplements with water or some other suitable physiologically innocuous inert liquid carrier or diluent, or mixtures thereof.

The compositions described above may be prepared by mixing the benzene derivatives of formula I with the inert physiologically innocuous carriers or diluents in any manner known to the art. Solid compositions are conveniently prepared by intimately mixing or dispersing the benzene derivatives uniformly throughout the feedstuffs or other solid carrier or diluent by methods such as grinding, stirring, milling or tumbling or by dissolving the benzene derivatives in a solvent, e.g. water or a suitable organic solvent, dispersing the solution so obtained in the feedstuff or other solid carrier or diluent and removing the solvent by any means known to the art. Medicated feedstuffs may also be prepared by mixing in concentrates or supplements containing higher concentrates of active ingredient to give feedstuffs throughout which the benzene derivatives are uniformly distributed at the desired concentration. The desired concentration of active ingredient in the compositions of the present invention is obtained by the selection of an appropriate ratio of the benzene derivatives to carrier or diluent.

Medicated feedstuffs will normally contain between 0.001 and 3% by weight of the benzene derivatives of formula I to give the required dosage. Concentrates and supplements will normally contain between 0.02 and 90%, preferably 0.1 to 50%, by weight of the benzene derivatives being, if desired, suitably diluted as hereinbefore described to give the required dosage.

Medicated animal feedstuffs, drinking water and other liquids normally consumed by the animals and compositions containing the benzene derivatives of formula I dispersed in, or admixed with, any other suitable inert carrier or diluent, as hereinbefore described, including concentrates or supplements, form further features of the present invention.

Anthelmintic compositions according to the present invention may also contain bacteriostats, bactericidal agents, sporicidal agents and pharmaceutically-acceptable colouring agents. The compositions may also contain, if desired, auxiliary therapeutic agents, for example fluke drugs such as 4-cyano-2-iodo-6-nitrophenol, hexachloroethane, carbon tetrachloride, 3,3',5,5',6,6'-hexachloro-2,2'-dihydroxydiphenylmethane, 2,2'-dihydroxy-3,3',5,5',6-pentachlorodiphenylmethane, 2,2'-dihydroxy-3,3',5,5',6-pentachlorobenzanilide, 2,2'-dihydroxy-3,3'-dinitro-5,5'-dichlorodiphenyl, bis[2-(4-acetamidophenoxy)ethyl] ether or 2-acetoxy-4'-chloro-3,5-diiodobenzanilide, 2-(4-thiazolyl)benzimidazole, 5(6)-isopropoxycarbonylamino-2-(4-thiazolyl)benzimidazole, methyl 5(6)-butyl-2-benzimidazolecarbamate, methyl 5(6)-benzoyl-2-benzimidazolecarbamate, 6-phenyl-2,3,5,6-tetrahydroimidazo[2,1-b]thiazole, trans-1,4,5,6-tetrahydro-1-methyl-2-(2-thiene-2'-ylvinyl)pyrimidine, phenothiazine, cyanacethydrazide, piperazine and its salts such as piperazine adipate, 1-diethylcarbamoly-4-methylpiperazine, tetrachloroethylene, 4,4'-dichloro-2,2'-dihydroxydiphenylmethane, N-(2-chloro-4-nitrophenyl)-5-chlorosalicylamide, N,N-dibutyl-4-hexyloxynaphthamidine, trans-1,4-bis-(2-isothiocyanatoethyl)cyclohexane and 1-styrylpyridinium salts, e.g. the bromide, embonate, amsonate or isethionate.

The new compounds of general formula I may be used as fungicides against fungi pathogenic to growing plants, seeds and fruits in the form of fungicidal compositions, suitable for use in agriculture, containing as active ingredient at least one of the benzene derivatives of general formula I in association with one or more diluents compatible with the benzene derivatives and suitable for use in fungicidal compositions. Preferably the compositions contain between 0.005% and 95% by weight of the compounds of general formula I. Suitable solid diluents include aluminium silicate, kieselguhr, tricalcium phosphate, powdered cork, absorbent carbon black, magnesium silicate, a clay such as kaolin, bentonite or attapulgite or a compatible solid wetting, dispersing or emulsifying agent. The compositions containing solid diluents, which may take the form of dusts or wettable powders, are prepared by impregnating the solid diluents with solutions of the compounds of general formula I in volatile solvents and evaporating the solvents, or by injecting those compounds of general formula I which are viscous liquids at room temperature, under high pressure into a suitable powderblender containing the solid diluent or diluents, and, if necessary, grinding the product so as to obtain powders.

The wetting, dispersing and emulsifying agents which may be present, particularly in wettable powders, may be of the ionic or non-ionic types, for example, sulphoricinoleates, quaternary ammonium derivatives or products based upon condensates of ethylene oxide with nonyl and octyl phenol, or fatty acid esters of anhydrosorbitols which have been rendered soluble by etherification of the free hydroxy groups by condensation with ethylene oxide, or mixtures of these types of agents. Wettable powders according to the present invention may be treated with water immediately before use to give suspensions ready for application.

Liquid compositions may take the form of solutions, suspensions, slurries and emulsions of the compounds of general formula I which may, if desired, incorporate wetting, dispersing or emulsifying agents. These emulsions, suspensions and solutions may be prepared using aqueous, organic or aqueous-organic diluents, for example acetophenne, isophorone, toluene, xylene and mineral, animal or vegetable oils (and mixtures of these diluents), which may contain wetting, dispersing or emulsifying agents of the ionic or non-inonic types or mixtures thereof, for example those of the types described above. When desired, the emulsions containing the compounds of general formula I may be used in the form of self-emulsifying concentrates containing the active substances dissolved in the emulsifying agents or in solvents containing emulsifying agents compatible with the active substance, the simple addition of water to such concentrates producing compositions ready for use. Fungicidal compositions in the form of aerosols containing the compounds of general formula I are also within the scope of the present invention. If desired, the fungicidal compositions according to the present invention may contain other adjuvants such as adhesives.

Agricultural compositions according to the present invention may also contain, as well as the compound or compounds of formula I, pesticides such as insecticides, for example γ-1,2,3,4,5,6-hexachlorocyclohexane, or other fungicides, for example 3a,4,7,7a-tetrahydro-N-(trichloromethanesulphenyl)phthalimide.

Accordingly, there is provided a method for the destruction of fungi pathogenic to plants which comprises the application of the fungicidal compositions comprising compounds of formula I, if necessary after suitable dilution, to crop-growing areas infested with these fungi. By the term 'crop-growing' is meant areas in which economically valuable crops are growing. Preferably the fungicidal compositions are applied at rates of from 0.25 to 3 lbs. of benzene derivative per acre, more particularly in the form of aqueous sprays prepared by diluting concentrates with water.

There is further provided a method for the protection of seeds against fungi which comprises the treatment of the seeds with the fungicidal compositions comprising compounds of the formula I, if necessary after dilution. Preferably the fungicidal compositions are applied to the seeds at rates of from 0.05 to 0.2% of benzene derivative, more particularly in the form of dry powder or slurry compositions.

There is further provided a method for the protection from fungi of fruits after harvest which comprises the treatment of the fruits with the fungicidal compositions comprising compounds of formula I, if necessary after dilution. Preferably the fungicidal compositions are applied to the fruits at rates of from 0.25 to 3.0 lb of benzene derivative per 100 gallons of water, more particularly in the form of a solution in which the fruits are dipped.

As a further feature of the invention, the new compounds of general formula I may be used as fungicides against fungi pathogenic to animals in the form of therapeutically useful compositions comprising at least one of the compounds in association with a pharmaceutically-acceptable carrier or coating of the type hereinbefore described as suitable for the use of compounds of general formula I as anthelmintics. Therapeutically useful compositions comprising at least one of the new compounds of general formula I for use against fungi pathogenic to animals may be formulations suitable for topical application, e.g. lotions, ointments or creams.

The following Composition Examples illustrate the formulation of therapeutically useful and fungicidal compositions including benzene derivatives of formula I.

It is to be understood that any other compound of formula I may be substituted for the compound specifically mentioned, bearing in mind that the proportions of the ingredients and methods of preparing the compositions may be modified in accordance with the physico-chemical properties of the compound of formula I used, such modification being readily carried out after simple experimentation by one skilled in the art of formulating therapeutically useful or fungicidal compositions.

COMPOSITION EXAMPLE 1

Tablets of the formula:

| | |
|---|---|
| 3-[2-(2-dimethylaminoacetamido)-4-phenylthiophenyl]-2-methoxycarbonyliminothiazolidin-4-one | 250 mg |
| lactose | 200 mg |
| starch | 50 mg |
| polyoxyethylene sorbitan monolaurate | 0.5 mg |
| magnesium stearate | 5 mg | were prepared by mixing the benzene derivative and the lactose with part of the starch and granulating with a 5% starch mucilage containing the polyoxyethylene sorbitan monolaurate.

The mixture was sifted through a 20 mesh British Standard sieve, dried, and the remainder of the starch, together with the magnesium stearate, was incorporated into the mixture. After a second sifting through a 20 mesh British Standard sieve the mixture was compressed into tablets.

COMPOSITION EXAMPLE 2

A solution for oral administration as an anthelmintic was obtained by dissolving 3-[2-(2-dimethylaminoacetamido)-4-phenylthiophenyl]-2-methoxycarbonyliminothiazolidin-4-one methanesulphonate (10 g) in water (100 ml).

This solution was sterilised by filtration through a bacteria-retaining filter to give a sterile composition suitable for parenteral administration as an anthelmintic.

COMPOSITION EXAMPLE 3

A wettable powder was made up from the following

| | |
|---|---|
| 3-[2-(2-dimethylaminoacetamido)-4-phenylthiophenyl]-2-methoxycarbonyliminothiazolidin-4-one | 75% w/w |
| diatomaceous earth | 15% w/w |
| micronised silica | 2% w/w |
| wetting agent (blend of polyoxyethylene alkyl ethers, polyoxyethylene fatty acids and their esters) | 8% w/w | by mixing the components and milling them in an air-jet miller.

COMPOSITION EXAMPLE 4

A wettable powder was made up from the following components:

| | |
|---|---|
| 3-[2-(2-dimethylaminoacetamido)-4-phenylthiophenyl]-2-methoxycarbonyliminothiazolidin-4-one | 52% w/w |
| finely-divided synthetic magnesium silicate | 39% w/w |
| micronised silica | 2% w/w |
| wetting agent (blend of polyoxyethylene alkyl ethers, polyoxyethylene fatty acids and their esters) | 7% w/w | by mixing the components and milling them in an air-jet miller.

COMPOSITION EXAMPLE 5

3-[2-(2-Dimethylaminoacetamido)-4-phenylthiophenyl]-2-methoxycarbonyliminothiazolidin-4-one (1g), previously sifted through a 40 mesh British Standard sieve, was packed into a gelatin capsule.

COMPOSITION EXAMPLE 6

A preparation for oral administration was obtained by mixing 3-[2-(2-dimethylaminoacetamido)-4-phenylthiophenyl[-2-methoxycarbonyliminothiazolidin-4-one (1 g), previously sifted through a 40 mesh British Standard sieve, and polyethylene glycol 6000 (10 g) at 50° C, and cooling to 25° C to obtain a gel.

COMPOSITION EXAMPLE 7

3-[2-(2-Dimethylaminoacetamido)-4-phenylthiophenyl]-2-methoxycarbonyliminothiazolidin-4-one (18 parts w/w) was added to wheat middlings (82 parts w/w) and intimately mixed to give a concentrate suitable for incorporation in an animal feedstuff at a rate sufficient to give an anthelmintically-effective amount of the benzene derivative in the feedstuff consumed by the animal.

COMPOSITION EXAMPLE 8

3-[2-(2-Dimethylaminoacetamido)-4-phenylthiophenyl]-2-methoxycarbonyliminothiazolidin-4-one (5 parts by weight) was added to limestone flour (20 parts w/w). The mixture was ground to give a concentrate suitable for incorporation in an animal feedstuff at a rate sufficient to give an anthelmintically-effective amount of the benzene derivative in the feedstuff consumed by the animal.

COMPOSITION EXAMPLE 9

A suspension for oral administration for use as an anthelmintic was obtained by mixing diethylcarbamazine citrate (4.4 g) and 3-[2-(2-dimethylaminoacetamido)-4-phenylthiophenyl]-2-methoxycarbonyliminothiazolidin-4-one (19.6 g of a 52% w/w wettable powder prepared as described in Composition Example 4) with water (140 ml).

COMPOSITION EXAMPLE 10

A suspension for oral administration for use as an anthelmintic was obtained by mixing 1-styrylpyridinium amsonate monohydrate (10 g) previously sifted through a 60 mesh British Standard sieve, and 3-[2-(2-dimethylaminoacetamido)-4-phenylthiophenyl]-2-methoxycarbonyliminothiazolidin-4-one (19.6 g of a 52% w/w wettable powder prepared as described in Composition Example 4) with water (140 ml).

COMPOSITION EXAMPLE 11

A solution for oral administration as an anthelmintic was obtained by dissolving 3-[2-(2-dimethylaminoacetamido)-4-phenylthiophenyl]-2-methoxycarbonyliminothiazolidin-4-one methanesulphonate (10 g) and 1-styrylpyridinium isethionate (10 g) in water (100 ml). This solution was sterilised by filtration through a bacteria-retaining filter to give a sterile composition suitable for parenteral administration as an anthelmintic.

COMPOSITION EXAMPLE 12

A solution for oral administration as an anthelmintic was obtained by dissolving diethylcarbamazine citrate (4.4 g) and 3-[2-(2-dimethylaminoacetamido)-4-phenylthiophenyl]-2-methoxycarbonyliminothiazolidin-4-one methanesulphonate (10 g) in water (100 ml). This solution was sterilised by filtration through a bacteria-retaining filter to give a sterile composition suitable for parenteral administration as an anthelmintic.

COMPOSITION EXAMPLE 13

A wettable powder was obtained by mixing

| | |
|---|---|
| 3-[2-(2-dimethylaminoacetamido)-4-phenylthiophenyl]-2-methoxycarbonyliminothiazolidin-4-one hydrochloride | 50 parts w/w |
| Texofor FX 500 (an alkylphenyl-polyoxyethylene condensate) | 10 parts w/w |
| Celite 281 (a finely-divided diatomaceous earth) | 40 parts w/w |
| in a ribbon-blender. | |

COMPOSITION EXAMPLE 14

A wettable powder was obtained by mixing:

| | |
|---|---|
| 3-[2-(2-dimethylaminoacetamido)-4-phenylthiophenyl]-2-methoxycarbonyliminothiazolidin-4-one hydrochloride | 50 parts w/w |
| Belloid TD (a polymethyl bis-naphthyl sodium sulphonate) | 10 parts w/w |
| Clarcelflo SAS (an expanded pearlite) | 35 parts w/w |
| Aerosil (a finely-divided silicon dioxide) | 5 parts w/w |
| in a ribbon-blender. | |

COMPOSITION EXAMPLE 15

A liquid concentrate in the form of a suspension was obtained by mixing:

| | |
|---|---|
| 3-[2-(2-dimethylaminoacetamido)-4-phenylthiophenyl]-2-methoxycarbonyliminothiazolidin-4-one hydrochloride | 60 parts w/w |
| bentonite | 3 parts w/w |
| Cutafor 09 (a polyethoxylated alkylamine) | 10 parts w/w |
| white spirit (a petroleum distillate) | 10 parts w/w |

COMPOSITION EXAMPLE 16

3-[2-(2-Dimethylaminoacetamido)-4-phenylthiophenyl]-2-methoxycarbonyliminothiazolidin-4-one (10 g) was dissolved in dimethyl sulphoxide (100 ml) to give a solution suitable for dermal or parenteral administration.

COMPOSITION EXAMPLE 17

A mineral lick was prepared in the usual manner from

| | |
|---|---|
| 3-[2-(2-dimethylaminoacetamido)-4-phenylthiophenyl]-2-methoxycarbonyliminothiazolidin-4-one | 2 parts w/w |
| sodium chloride | 195 parts w/w |
| other minerals (e.g. magnesium compounds and phosphorus compounds) and vitamins known to be desirable in the diet of animals. | 3 parts w/w |

COMPOSITION EXAMPLE 18

A liquid food supplement was prepared from

| | |
|---|---|
| 3-[2-(2-dimethylaminoacetamido)-4-phenylthiophenyl]-2-methoxycarbonyliminothiazolidin-4-one | 1 part w/w |
| molasses | 650 parts w/w |
| water | 349 parts w/w |

COMPOSITION EXAMPLE 19

Drinking water was treated so as to render it suitable for continuous medication of animals by dissolving therein 3-[2-(2-dimethylaminoacetamido)-4-phenylthiophenyl]-2-methoxycarbonyliminothiazolidin-4-one hydrochloride (0.01% w/w).

COMPOSITION EXAMPLE 20

3-[2-(2-Dimethylaminoacetamido)-4-phenylthiophenyl[-2-methoxycarbonyliminothiazolidin-4-one (250 parts w/w) was combined with Atlox 4855 (6 parts w/w) and Aerosil 200 (1 part w/w) and water (to 500 parts w/w) and the mixture was passed through a colloid mill, to give a slurry suitable for use as a seed-dressing.

Atlox 4855 is a polyoxyethylene triglyceride/alkyl aryl sulphonate blend and Aerosil 200 is microfine silicon dioxide.

COMPOSITION EXAMPLE 21

3-[2-(2-Dimethylaminoacetamido)-4-phenylthiophenyl]-2-methoxycarbonyliminothiazolidin-4-one hydrochloride (0.4 lb) was dissolved in water (100 gallons) to form a solution suitable for use as a post-harvest dip for fruits.

We claim:

1. A benzene derivative of the formula:

[Structure I: benzene ring with $R^2$ substituent, connected to a heterocyclic ring containing N, S, with O=B group, N—COOR$^1$, and NHCOAZ substituent]

wherein $R^1$ is alkyl of 1 through 4 carbon atoms, $R^2$ is —$SR^3$, —$SOR^3$, —$SO_2R^3$ or —$OR^3$, where $R^3$ is alkyl of 1 through 6 carbon atoms, allyl, phenyl, benzyl, cyclopentyl, or cyclohexylmethyl, the position of $R^2$ on the benzene ring being either para to the group —NHCOAZ or para to the heterocyclo group shown in the formula, A is a bivalent straight-chain aliphatic hydrocarbon radical of 1 through 4 carbon atoms or a said hydrocarbon radical substituted by at least one methyl group, Z is a group of the formula:

$$-N\begin{array}{c}R^4\\ \diagup\\ \diagdown\\ R^6\end{array}\!\!\!\!-R^{5\oplus}\cdot X^\ominus \quad \text{or} \quad -N\begin{array}{c}R^5\\ \diagup\\ \diagdown\\ R^6\end{array}$$

II              III wherein $R^4$ is hydrogen or alkyl or 1 through 4 carbon atoms, $R^5$ and $R^6$ are each methyl or ethyl, and $X^-$ represents a pharmaceutically acceptable or agriculturally acceptable anion, and B represents a bivalent methylene or ethylene group, or a bivalent methylene or ethylene group substituted by at least one methyl group.

2. A benzene derivative according to claim 1 wherein $R^1$ represents methyl.

3. A benzene derivative according to claim 1 wherein the group represented by $R^2$ is para to the heterocyclo group in the formula depicted in claim 1.

4. A benzene derivative according to claim 1 wherein Z represents a grouping of formula II depicted in claim 1.

5. A benzene derivative according to claim 1 wherein Z represents a grouping of formula II depicted in claim 1 and $X^-$ in that formula represents a chloride or methanesulphonate ion.

6. A benzene derivative according to claim 1 wherein $R^1$ is methyl or ethyl, $R^2$ is —$SR^3$ or —$SOR^3$, where $R^3$ is as defined in claim 32, A is methylene or ethylene, B is methylene, and Z is a group of the formula:

$$-N\begin{array}{c}R^4\\ \diagup\\ \diagdown\\ R^6\end{array}\!\!\!\!-R^{5\oplus}\cdot X^\ominus \quad \text{or} \quad -N\begin{array}{c}R^5\\ \diagup\\ \diagdown\\ R^6\end{array}$$

II              III $R^4$ represents hydrogen, $X^-$ is as defined in claim 32, and $R^5$ and $R^6$ in formulae II and III are each methyl or ethyl.

7. A benzene derivative according to claim 6 wherein $R^1$ represents methyl.

8. A benzene derivative according to claim 1 wherein $R^2$ represents a group of the formula —$SR^3$ wherein $R^3$ is as defined in claim 1.

9. A benzene derivative according to claim 8 wherein $R^3$ represents alkyl of 1 through 3 carbon atoms.

10. A benzene derivative according to claim 6, wherein Z represents a group of the formula:

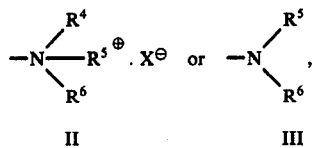

$R^4$ represents hydrogen and $X^-$ represents a chloride or methanesulphonate ion, and $R^5$ and $R^6$ in formulae II and III represent methyl or ethyl.

11. A benzene derivative according to claim 1 wherein $R^1$ represents methyl, $R^2$ represents phenylthio or ethylthio, A represents methylene, B represents methylene, Z represents a group of the formula:

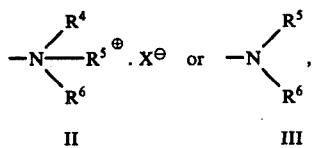

$R^4$ represents hydrogen and $X^-$ is as defined in claim 1, and $R^5$ and $R^6$ in formulae II and III represent methyl or ethyl.

12. A benzene derivative according to claim 11 wherein $X^-$ represents a chloride or methanesulphonate ion.

13. A benzene derivative according to claim 1 which is 3-[2-(2-dimethylaminoacetamido)-4-phenylthiophenyl]-2-methoxycarbonyliminothiazolidin-4-one, or a salt thereof having present a pharmaceutically acceptable or agriculturally acceptable anion.

14. A benzene derivative according to claim 1 which is 3-[4-ethylthio-2-(2-dimethylaminoacetamido)phenyl]-2-methoxycarbonyliminothiazolidin-4-one, or a salt thereof having present a pharmaceutically acceptable or agriculturally acceptable anion.

15. A benzene derivative according to claim 1 which is 3-[2-(2-diethylaminoacetamido)-4-phenylthiophenyl]-2-methoxycarbonyliminothiazolidin-4-one, or a salt thereof having present a pharmaceutically acceptable or agriculturally acceptable anion.

16. A benzene derivative according to claim 1 which is 3-[2-(2-dimethylaminoacetamido)-5-phenylthiophenyl]-2-methoxycarbonyliminothiazolidin-4-one, or a salt thereof having present a pharmaceutically acceptable or agriculturally acceptable anion.

17. A benzene derivative according to claim 1 which is 3-[4-allylthio-2-(2-dimethylaminoacetamido)phenyl]-2-methoxycarbonyliminothiazolidin-4-one, 3-[4-cyclohexylmethylthio-2-(2-dimethylaminoacetamido)phenyl]-2-methoxycarbonyliminothiazolidin-4-one, 3-[4-n-butylthio-2-(2-dimethylaminoacetamido)phenyl]-2-methoxycarbonyliminothizaolidin-4-one, 3-[4-benzylthio-2-(2-dimethylaminoacetamido)phenyl]-2-methoxycarbonyliminothiazolidin-4-one, 3-[4-cyclopentylthio-2-(2-dimethylaminoacetamido)phenyl]-2-methoxycarbonyliminothiazolidin-4-one, 3-[2-(2-dimethylaminoacetamido)-4-n-pentylthiophenyl]-2-methoxycarbonyliminothiazolidin-4-one, 3-[2-(2-dimethylaminoacetamido)-4-n-propylthiophenyl]-2-methoxycarbonyliminothiazolidin-4-one, 3-[2-(3-dimethylaminopropionamido)-4-phenylthiophenyl]-2-methoxycarbonyliminothiazolidin-4-one, or a salt of a said benzene derivative having present a pharmaceutically acceptable or agriculturally acceptable anion.

* * * * *